(12) United States Patent
Sharpless et al.

(10) Patent No.: US 6,276,145 B1
(45) Date of Patent: Aug. 21, 2001

(54) AEROSTATIC CT SUSPENSION

(75) Inventors: Ronald Bryan Sharpless, South Euclid; William Charles Brunnett, Concord, both of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/428,431

(22) Filed: Oct. 27, 1999

(51) Int. Cl.[7] .................. F25B 19/00; F25D 15/00; F25D 23/12
(52) U.S. Cl. .................. 62/51.1; 62/331; 62/259.2; 378/15
(58) Field of Search .................. 378/4, 15; 62/51.1, 62/331, 259.2

(56) References Cited

U.S. PATENT DOCUMENTS

| | | | |
|---|---|---|---|
| 4,618,789 | * 10/1986 | Fliskowski | 310/13 |
| 4,709,559 | * 12/1987 | Dotzauer et al. | 62/499 |
| 5,610,968 | 3/1997 | Deucher et al. | 378/199 |
| 5,628,918 | * 5/1997 | Mastalski | 216/8 |

FOREIGN PATENT DOCUMENTS 04371141  12/1992 (JP).

* cited by examiner

*Primary Examiner*—William Doerrler
(74) *Attorney, Agent, or Firm*—Fay, Sharpe, Fagan, Minnich & McKee, LLP (57) ABSTRACT

A CT scanner (10) for obtaining a medical diagnostic image of a subject includes a stationary gantry (12), and a rotating gantry (16) rotatably supported on the stationary gantry (12) for rotation about the subject. A fluid bearing (18) is interposed between the stationary and rotating gantries (12) and (16), respectively. The fluid bearing (18) provides a fluid barrier (110) which separates the rotating gantry (16) from the stationary gantry (12). In a preferred embodiment, the fluid bearing (18) provides for quieter CT scanner operation at high rotational speeds. Moreover, eliminating the physical contact between the gantries minimizes wear and optimizes longevity.

19 Claims, 6 Drawing Sheets

AEROSTATIC CT SUSPENSION

BACKGROUND OF THE INVENTION

The present invention relates to the art of medical diagnostic imaging. It finds particular application in conjunction with computed tomography (CT) scanners, and will be described with particular reference thereto. However, it is to be appreciated that the present invention is also amenable to other like applications.

Generally, CT scanners have a defined examination region or scan circle in which a patient, phantom or like subject being imaged is disposed. A thin beam of radiation is transmitted across the examination region from an radiation source, such as an x-ray tube, to oppositely disposed radiation detectors. The source, or beam of radiation, is rotated around the examination region while data is collected from the radiation detectors receiving x-ray radiation passing through the examination region and the subject disposed therein. Rotation of the radiation source is often achieved by mounting the radiation source to a rotating gantry which is rotated on a stationary gantry.

The sampled data is typically manipulated via appropriate reconstruction processors to generate an image representation of the subject which is displayed in a human-viewable form. Commonly, the x-ray data is transformed into the image representation utilizing filtered back projection. A family of rays extending from source to detector is assembled into a view. Each view is filtered or convolved with a filter function and backprojected into an image memory. Various view geometries have been utilized in this process. In a rotating, fan-beam-type scanner in which both the source and detectors rotate (i.e. a third generation scanner), each view is made up of concurrent samplings of an arc of detectors which span the x-ray beam when the x-ray source is in a given position to produce a source fan view. Alternately, with stationary detectors and a rotating source (i.e. a fourth generation scanner), a detector fan view is formed from the rays received by a single detector array as the x-ray source passes behind the examination region opposite the detector.

In any event, accurate reconstruction is dependant upon acquiring data views from a range of accurately resolved angular orientations or positions of the source as it rotates about the examination region. Reconstruction algorithms have been developed which use data collected over numerous helical rotations, 360 degrees of source rotation, 180 degrees plus the angle or spread of the fan of radiation, and the like. Therefore, scan times are constrained by the speed of rotation of the source.

In previously developed CT scanners, commonly the rotating gantry is supported on the stationary gantry via a mechanical bearing including rolling elements or balls interposed between two raceways. However, with increased rotational speed of the rotating gantry, noise levels associated which such mechanical bearings reach unacceptable levels. In continuously rotating systems, friction related heating can restrict the length of scans. Moreover, the accompanying friction causes wearing of parts in physical contact with one another thereby incurring disadvantageous maintenance requirements and a limited lifetime.

In another type of CT scanner, the rotating gantry is suspended via electromagnetic levitation. However, such a technique tends to be unstable and employs complex feedback controls to maintain stability. Moreover, the size and cost associated with such a system can be prohibitive when rotating loads of the size desired for many CT scanners, e.g., in the neighborhood of 1000 lbs.

The present invention contemplates a new and improved gantry suspension technique which overcomes the above-referenced problems and others.

SUMMARY OF THE INVENTION

In accordance with one aspect of the present invention, a CT scanner for obtaining a medical diagnostic image of a subject is provided. The CT scanner includes a stationary gantry, and a rotating gantry rotatably supported on the stationary gantry for rotation about the subject. A fluid bearing is interposed between the stationary and rotating gantries. The fluid bearing provides a fluid barrier which separates the rotating gantry from the stationary gantry.

In accordance with a more limited aspect of the present invention, the fluid barrier is a gas.

In accordance with a more limited aspect of the present invention, the gas is air.

In accordance with a more limited aspect of the present invention, the fluid barrier is a liquid.

In accordance with a more limited aspect of the present invention, the liquid is oil.

In accordance with a more limited aspect of the present invention, the CT scanner further includes a reservoir containing the fluid which is supplied from the reservoir to the fluid bearing to create the fluid barrier.

In accordance with a more limited aspect of the present invention, the fluid is supplied to the fluid bearing through distribution pads which distribute the fluid between the stationary and rotating gantries.

In accordance with a more limited aspect of the present invention, the distribution pads have a beveled edge along a leading side thereof relative to a direction of rotation of the rotating gantry.

In accordance with a more limited aspect of the present invention, the CT scanner further includes opposing surfaces on the stationary and rotating gantries which face one another across the fluid barrier. The opposing surfaces define the shape of the fluid bearing.

In accordance with a more limited aspect of the present invention, the shape of the fluid bearing is symmetrical with respect to an axial plane which is normal to an axis of rotation of the rotating gantry.

In accordance with a more limited aspect of the present invention, the shape of the fluid bearing is defined by two conic sections which meet at the axial plane to form an annular V-shaped trough.

In accordance with a more limited aspect of the present invention, the CT scanner further includes a recovery system which collects fluid escaping from the fluid bearing.

In accordance with a more limited aspect of the present invention, the CT scanner further includes a radiation source attached to the rotating gantry. The radiation source produces a beam of penetrating radiation which irradiates the subject as the rotating gantry rotates. A cooling system circulates a cooling fluid past the radiation source. The cooling fluid draws heat from the radiation source as the cooling fluid is circulated past the radiation source. A heat exchanger, interfacing the cooling system with the recovery system, transfers heat from the cooling fluid in the cooling system to the fluid collected by the recovery system.

In accordance with a more limited aspect of the present invention, the recovery system returns fluid collected thereby to the fluid bearing.

In accordance with another aspect of the present invention, a method of rotating a source of radiation about an axis is provided. The method includes suspending a second gantry from a first gantry while the second gantry has the source of radiation mounted thereto. Thereafter, a fluid is fed in between the first and second gantries such that they are spaced apart from one another by a layer of the fluid, and the second gantry is then rotated.

In accordance with a more limited aspect of the present invention, the method further includes controlling the rate at which the fluid is fed in between the first and second gantries.

In accordance with a more limited aspect of the present invention, the method further includes storing a reserve of the fluid such that the fluid is fed in between the first and second gantries from the stored reserve.

In accordance with a more limited aspect of the present invention, the method further includes generating dynamic forces which radially stabilize the second gantry as it rotates.

In accordance with a more limited aspect of the present invention, the method further includes collecting the fluid as it escapes from in between the first and second gantries, and returning the fluid for further use.

In accordance with a more limited aspect of the present invention, the method further includes transferring heat from a cooling fluid which cools the radiation source to the collected fluid.

One advantage of the present invention is faster CT scanner speeds and correspondingly reduced scan times.

Another advantage of the present invention is quieter CT scanner operation.

Yet another advantage of the present invention is extended bearing life with reduced maintenance due to the elimination of frictional wearing of contacting parts.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
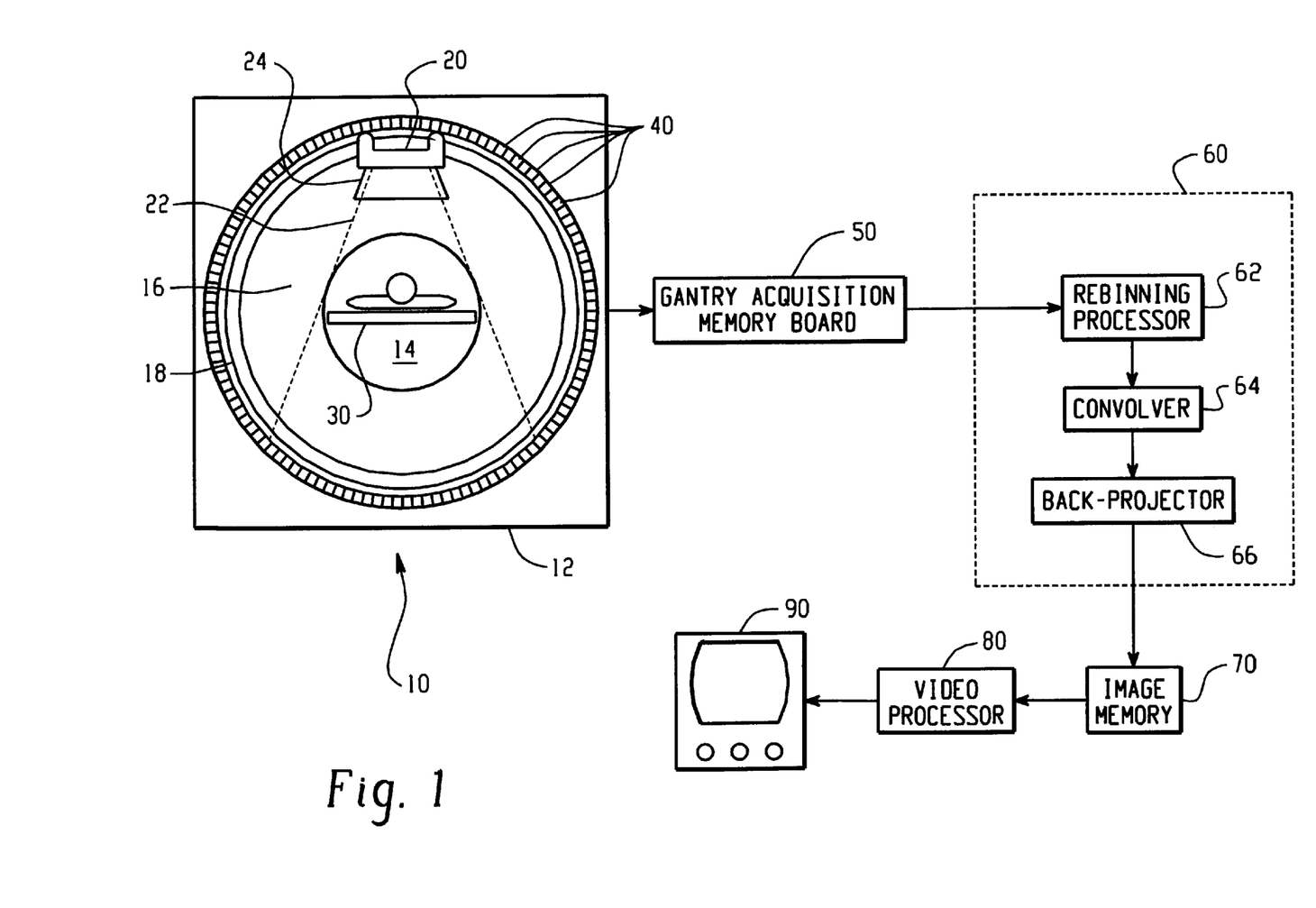
FIG. 1 is a diagrammatic illustration of a CT scanner in accordance with aspects of the present invention.

With reference to FIG. 1, a CT scanner 10 includes a first stationary gantry 12 which defines an examination region 14. A second rotating gantry 16 is suspended from or otherwise supported on the stationary gantry 12 by a fluid bearing 18 for rotation about the examination region 14. A radiation source 20, such as an x-ray tube, is arranged on the rotating gantry 16 for rotation therewith. The radiation source 20 produces a beam of penetrating radiation 22 that passes through the examination region 14 as the rotating gantry 16 rotates. A collimator and shutter assembly 24 forms the beam of penetrating radiation 22 into a thin fan shape and selectively gates the beam 22 on and off. Alternately, the radiation beam 22 is gated on and off electronically at the source 20. In any event, a subject support 30, such as a couch or the like, suspends or otherwise holds a subject being examined or imaged at least partially within the examination region 14 such that the fan-shaped beam of radiation 22 cuts a cross-sectional slice through the region of interest of the subject.

Optionally, the subject is successively re-positioned such that neighboring cross-sectional slices are taken in consecutive indexed fashion to produce a three-dimensional volume of slices. Alternately, as is the case with continuous helical CT, concurrently with the rotation of the second gantry 16, the support 30, and consequently the subject thereon, are translated along a central horizontal axis of the examination region 14. In this manner, the source 20 follows a helical path relative to the subject. In another preferred embodiment, the support 30 remains stationary while the first gantry 12 is translated or otherwise moved relative to the subject such that the source 20 follows a helical path relative thereto.

In the illustrated fourth generation CT scanner, a ring of radiation detectors 40 is mounted peripherally around the examination region 14 on the stationary gantry 12. Alternately, a third generation CT scanner is employed with an arc of radiation detectors 40 mounted on the rotating gantry 16 on a side of the examination region 14 opposite the source 20 such that they span the arc defined by the fan-shaped beam of penetrating radiation 22. Regardless of the configuration, the radiation detectors 40 are arranged to receive the radiation emitted from the source 20 after it has traversed the examination region 14.

In a source fan geometry, an arc of detectors which span the radiation emanating from the source 20 are sampled concurrently at short time intervals as the source 20 rotates behind the examination region 14 to generate a source fan view. In a detector fan geometry, each detector is sampled a multiplicity of times as the source 20 rotates behind the examination region 14 to generate a detector fan view. The paths between the source 20 and each of the radiation detectors 40 are denoted as rays.

The radiation detectors 40 convert the detected radiation into electronic projection data. That is to say, each of the radiation detectors 40 produces an output signal which is proportional to an intensity of received radiation. Optionally, a reference detector may detect radiation which has not traversed the examination region 14. A difference between the magnitude of radiation received by the reference detector and each radiation detector 40 provides an indication of the amount of radiation attenuation along a corresponding ray of a sampled fan of radiation. In either case, each radiation detector 40 generates data elements which correspond to projections along each ray within the view. Each element of data in the data line is related to a line integral taken along its corresponding ray passing through the subject being reconstructed.

With detector view geometry, each view or data line represents a fan of rays having its apex at one of the radiation detectors 40 collected over a short period of time as the source 20 rotates behind the examination region 14 from the detector. With source view geometry, each view or data line represents a fan of rays having an apex at the source 20 collected by concurrent sampling of all the radiation detectors 40 spanning the fan of radiation.

A gantry acquisition memory board 50-receives the sampled data from the radiation detectors 40. The gantry acquisition memory board 50 optionally shuffles the data to transform it from a detector fan geometry to a source fan geometry, or vice versa, and performs a ripple filtering operation before passing the data to an image processor 60 which reconstructs image representations of the subject.

The image processor 60 processes the data from the gantry acquisition memory board 50 and backprojects it into an image memory 70. More specifically, the image processor 60 performs mathematical manipulations which convolve each data set with an appropriate filter or convolution function for the view format. The image processor 60 of the preferred embodiment includes a convolver 64 which convolves the data sets and a backprojector 66 which backprojects the convolved data sets into the image memory 70. Ultimately, a video processor 80 selectively retrieves slices, projections, three-dimensional (3D) renderings, and other image information from the image memory 70 and appropriately formats an image representation for depiction on a human viewable display 90, such as a video monitor or the like.

Optionally, for those applications wherein other than parallel projection data is collected, the image processor 60 includes a rebinning processor 62. Initially, the electronic data generated by the radiation detectors 40 and sampled by the gantry acquisition memory board 50 is fed to the rebinning processor 62. The rebinning processor 62 converts each data line from its fan-beam or otherwise divergent format to a parallel-beam format. Thereafter, the image processor 60 implements a conventional reconstruction algorithm, such as a convolution and filtered back projection algorithm. Examples of suitable image processing techniques which are optionally employed (including back projection, rebinning, and other reconstruction techniques) are found in commonly owned U.S. Pat. Nos. 4,965,726; 5,262,946; 5,384,861; 5,396,418; 5,481,583; 5,485,493; and 5,544,212; all incorporated herein by reference.

Figure 2A:
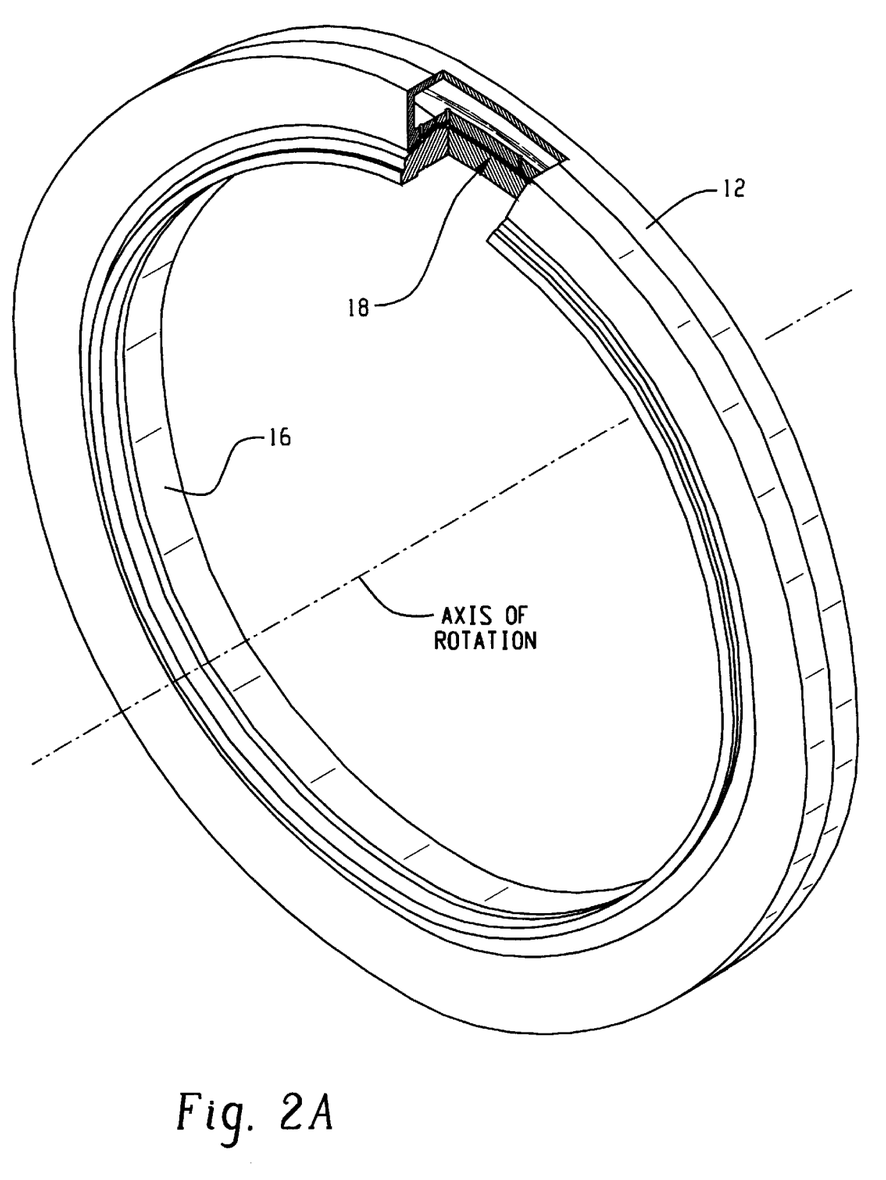
FIG. 2A is a partially cut away diagrammatic illustration showing the interface of rotating and stationary gantries of a CT scanner in accordance with aspects of the present invention.
Figure 2B:
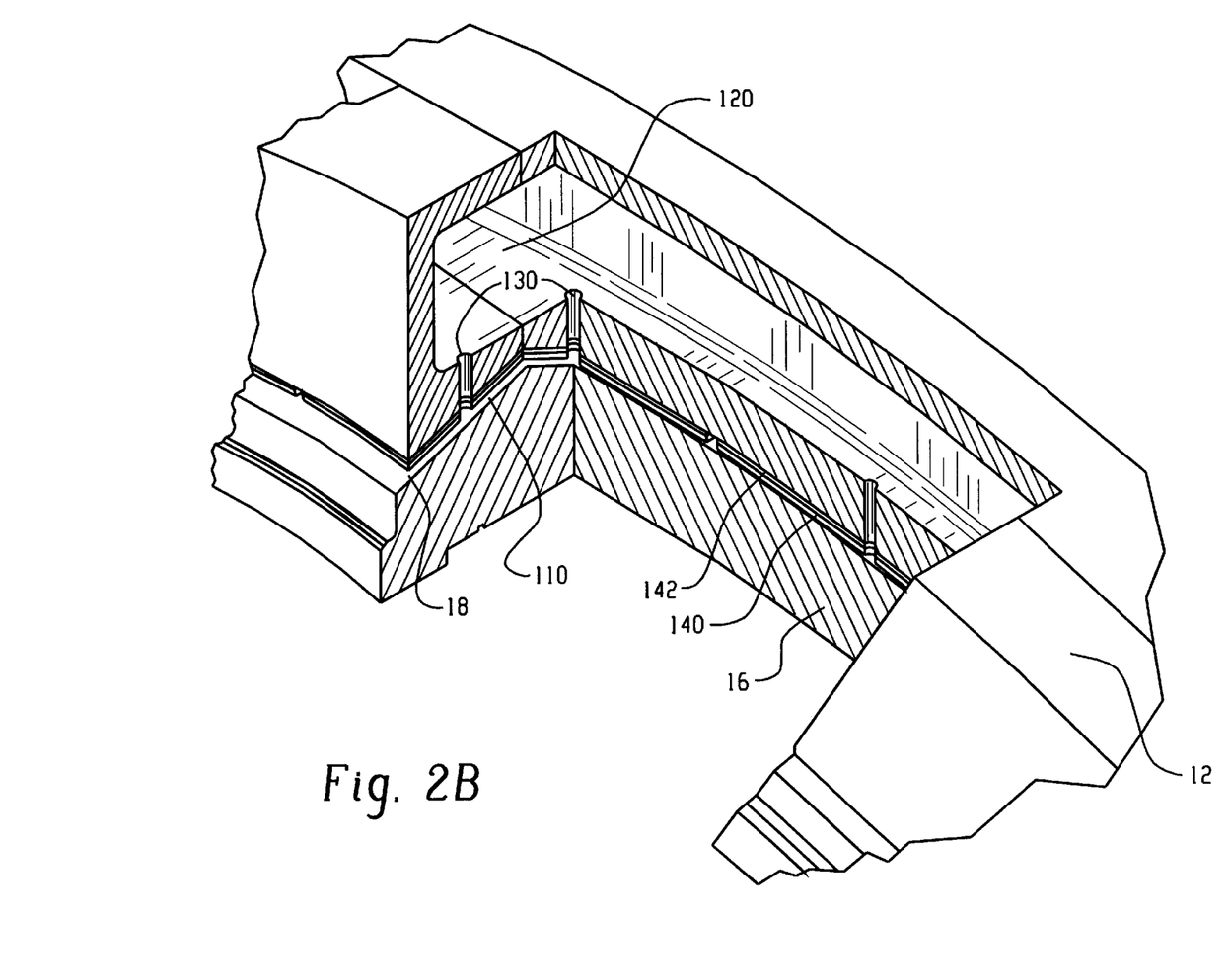
FIG. 2B is enlarged view of the partially cut away portion shown in FIG. 2A.
Figure 3:
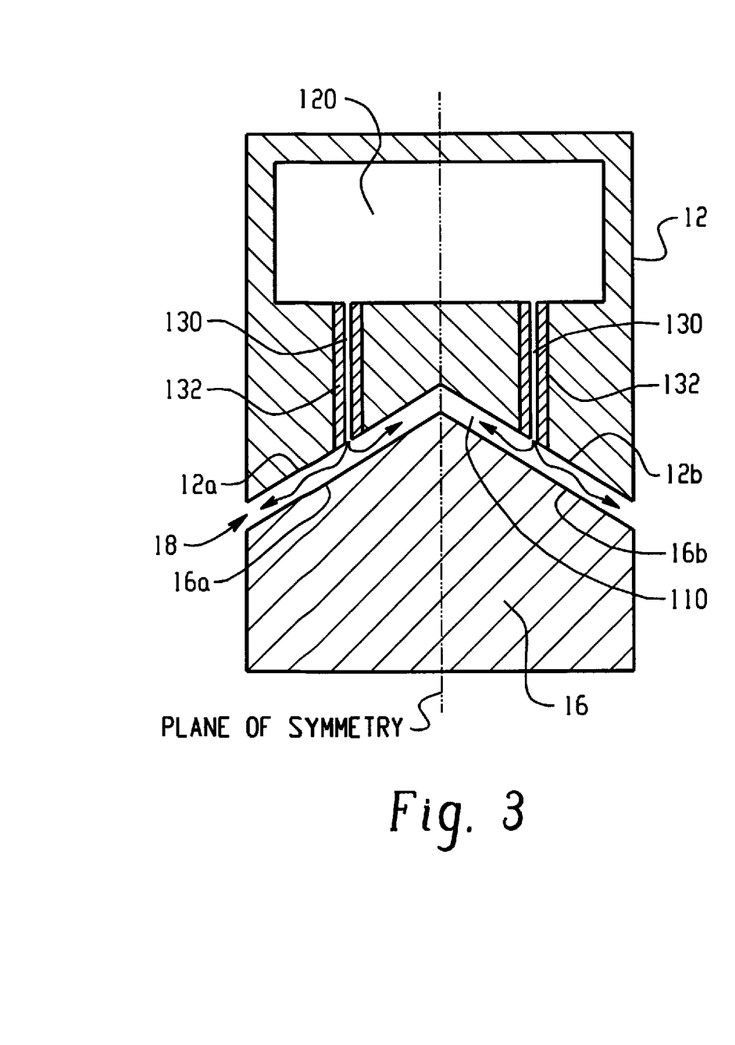
FIG. 3 is a cross-sectional view showing a fluid bearing in accordance with aspects of the present invention.

With reference to FIGS. 2A, 2B, and 3 and continuing reference to FIG. 1, in a preferred embodiment, the stationary gantry 12 and rotating gantry 16 suspended thereon interface with one another through a fluid bearing 18 interposed therebetween. The fluid bearing 18 provides a thin layer of fluid or a fluid barrier 110 that separates opposing surfaces of the stationary gantry 12 and rotating gantry 16. Surfaces 12a and 12b of the stationary gantry 12 and surfaces 16a and 16b of the rotating gantry 16 face one another respectively across the fluid barrier 110 in spaced apart relation such that the shape of the fluid bearing 18 is defined thereby. In preferred embodiments, for example, the gap between gantries or the thickness of the fluid barrier 110 is approximately 0.0175–0.03 mm with the larger thicknesses being employed in conjunction larger diameter rotating gantries. Optionally, the fluid is gas or alternately liquid. More specifically, the fluid is air or oil. Regardless, in this manner, the rotating gantry 16 is freely rotated while being suspended from the stationary gantry 12 without direct contact of the gantries and without any ball bearings, roller bearings, or other mechanical bearings being interposed therebetween.

In a preferred embodiment, a fluid stored under pressure in a reservoir 120 is fed or supplied to the fluid bearing 18 to create the fluid barrier 110. In one preferred embodiment, a pressure of approximately 690 kPa is used in conjunction with a gas fluid (e.g., air). Alternately, with a liquid fluid (e.g., oil) less pressure is employed. The fluid reserves and pressure are maintained in the reservoir 120 via a fluid pump which supplies the fluid thereto. As a safety feature, in the case of system failure, malfunction or other sudden system shutdown, the reserve fluid supply stored in the reservoir 120 is maintained at a level sufficient to continue suspension of the rotating gantry 16 until it comes to rest.

The fluid from the reservoir 120 is fed or supplied to the fluid bearing 18 through an array of orifices 130 circumferentially arranged about the fluid bearing 18. The orifices 130 provide for fluid communication between the reservoir 120 and the fluid bearing 18. Preferably, orifice inserts 132 having selected inner diameters are secured within the orifices 130 to limit or control the fluid flow therethrough. In a preferred embodiment, the orifice inserts 132 have an inner diameter of approximately 0.2 mm. Alternately, variable aperture valves, porous material inserts, or other like controls are used to adjust fluid flow to the desired level. Additionally, slot feeds are optionally substituted for the orifices 130.

Figure 4A:
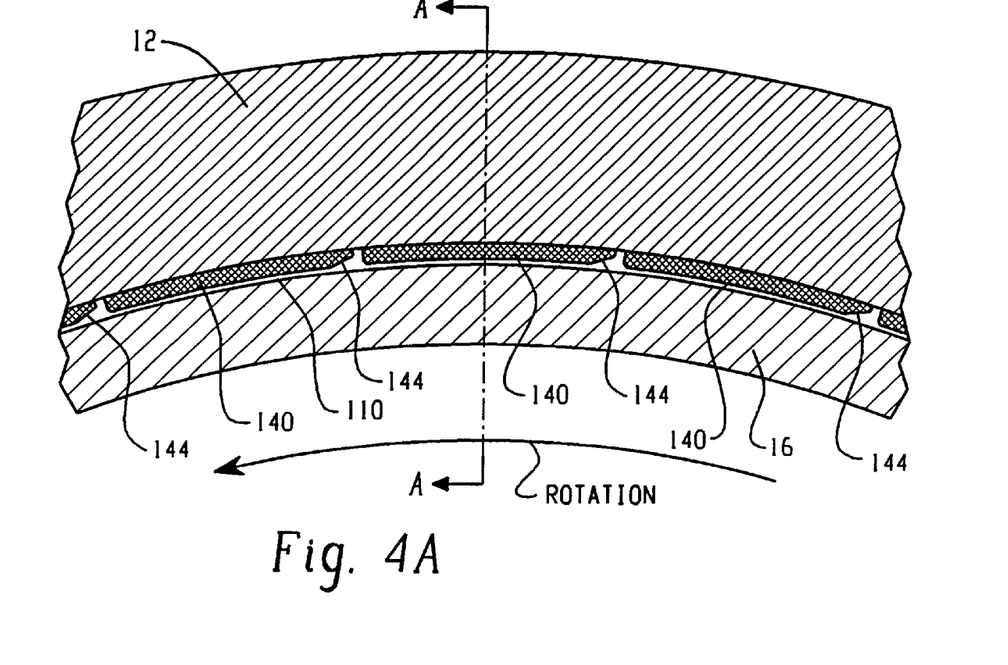
FIG. 4A is a partial side view of a fluid bearing in accordance with aspects of the present invention.
Figure 4B:
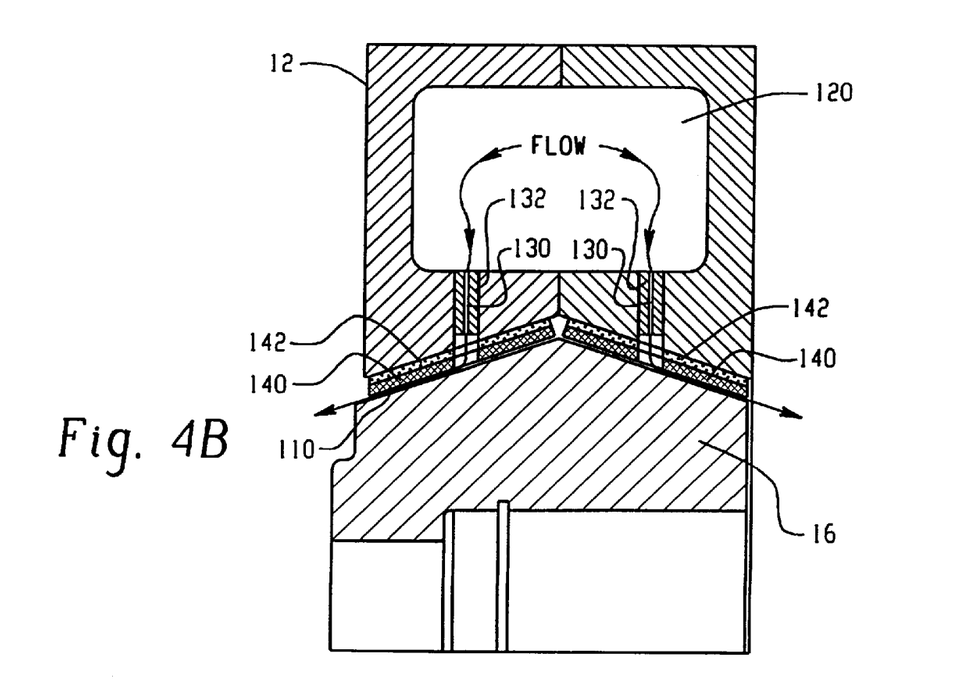
FIG. 4B is a cross-sectional view taken along section line A—A in FIG. 4A.

With further reference to FIGS. 4A and 4B, in a preferred embodiment, the stationary gantry 16 includes distribution pads 140 which are arranged around the gantry's inner diameter. The pads 140 are optionally secured by a layer of adhesive 142. As the fluid is being supplied through the orifices 130, it encounters and traverses the distribution pads 140 which diffuse and distribute the fluid into the fluid bearing 18 to create the fluid barrier 110. Preferably, the pads 140 are made of a porous medium or a rigid web of, e.g., carbon or other suitable material, which evenly distributes the fluid flow over its surface.

Optionally, as best seen in FIG. 4A, the distribution pads 140 have a beveled, sloped, or otherwise angled edge 144 along a leading side thereof relative to the direction of rotation of the rotating gantry 16. The angled edges 144 generate a desired pressure distribution or aerodynamic/hydrodynamic forces which stiffen and stabilize the rotating gantry 16 against radial forces thereby restricting lateral movement of the axis of rotation of the rotating gantry 16.

In a preferred embodiment, the shape of the fluid bearing 18 is symmetrical with respect to an axial plane which is normal to the axis of rotation of the rotating gantry 16. See FIG. 3. More specifically, the shape of the fluid bearing 18 is defined by two conic sections which meet at the axial plane to form an annular V-shaped trough. In this manner, the sloping conic sections of the fluid bearing 18 serve to stiffen and stabilize the rotating gantry 16 against axial forces thereby restricting the position and orientation of the rotating gantry 16 to the axial plane in which it rotates. That is to say, the axial forces experienced by surfaces 16a and 16b of the rotating gantry 16, due to the radial feeding of fluid under pressure to the bearing 18, tends to center the rotating gantry 16 in the track formed by surfaces 12a and 12b of the stationary gantry 12.

As the fluid flows into the channel to create fluid barrier 110, the flow splits. Fluid flowing toward the apex where there is no fluid outlet forms a high pressure or maximum lift zone.

The fluid pressures are self-centering. That is, if the rotating gantry 16 should start to shift parallel to its axis of rotation, the channel and hence fluid barrier 110 will become narrower in the direction of travel. Narrowing of the channel in the direction of travel increases the pressure while widening the other side of the channel reduces pressure. This pressure differential creates a force which urges the rotating gantry 16 back toward its original center.

Figure 5:
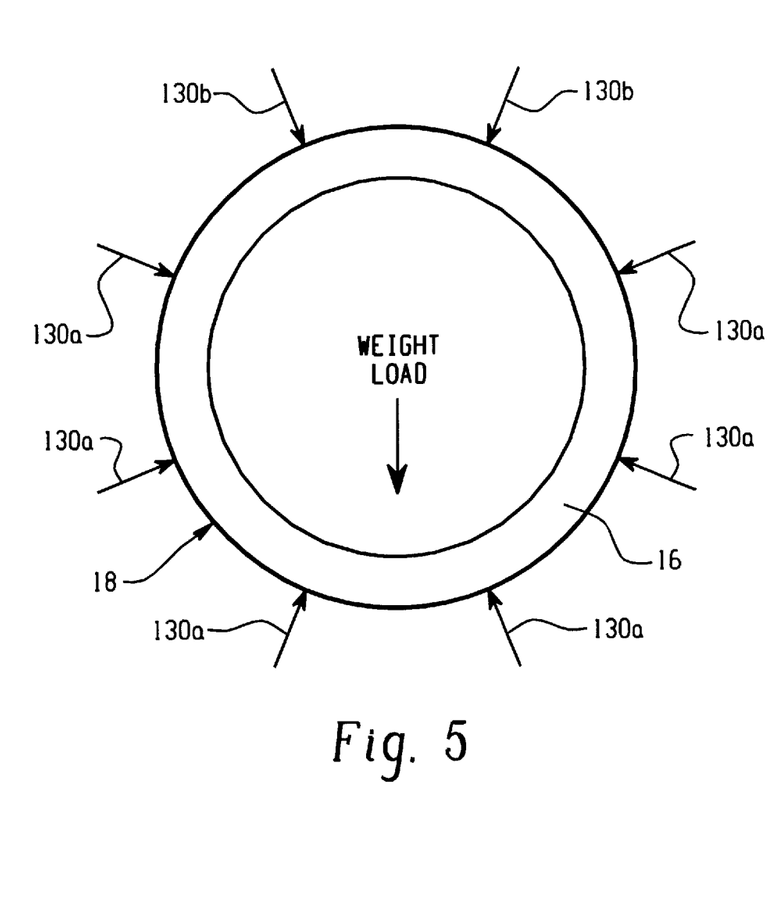
FIG. 5 is a diagrammatic illustration showing asymmetric feeding of a fluid bearing in accordance with aspects of the present invention; and, FIG. 6 is a diagrammatic illustration of a CT scanner with fluid recover system in accordance with aspects of the present invention.

In a preferred embodiment, to counter the weight of the load (i.e., the weight of the rotating gantry 16 and attached components), fluid is asymmetrically fed to the fluid bearing 18 by asymmetrically locating the orifices 130 circumferentially around the fluid bearing 18 and/or by asymmetrically controlling the fluid flows through the orifices 130. To provide lift, more fluid is fed to the fluid bearing 18 from beneath the rotating gantry 16 than from above. In a preferred embodiment, for example, as shown in FIG. 5, a net lift is provided by having fluid fed to the fluid bearing 18 from feed points 130a while no fluid is fed from above the rotating gantry 16 at feed points 130b. Likewise, the beveled edges 144 on the distribution pads 140 are asymmetrically arranged and/or the angle of the bevels are asymmetrically selected to generate or provide aerodynamic/hydrodynamic forces with a net positive lift acting on the rotating ring 16. Optionally, the asymmetric arrangement of fluid feed and asymmetric arrangement of bevels are employed in lieu of or in conjunction with one another to achieve the desire lift which counters the weight of the load. Baffles are also optionally added adjacent to annular discharge areas of the channel defining the fluid barrier 110 to increase pressure, at least at selected locations. Analogously, an air outlet passage is optionally tapped into the high pressure zone at the apex of the fluid barrier 110 in regions where relative pressure is to be reduced.

Figure 6:
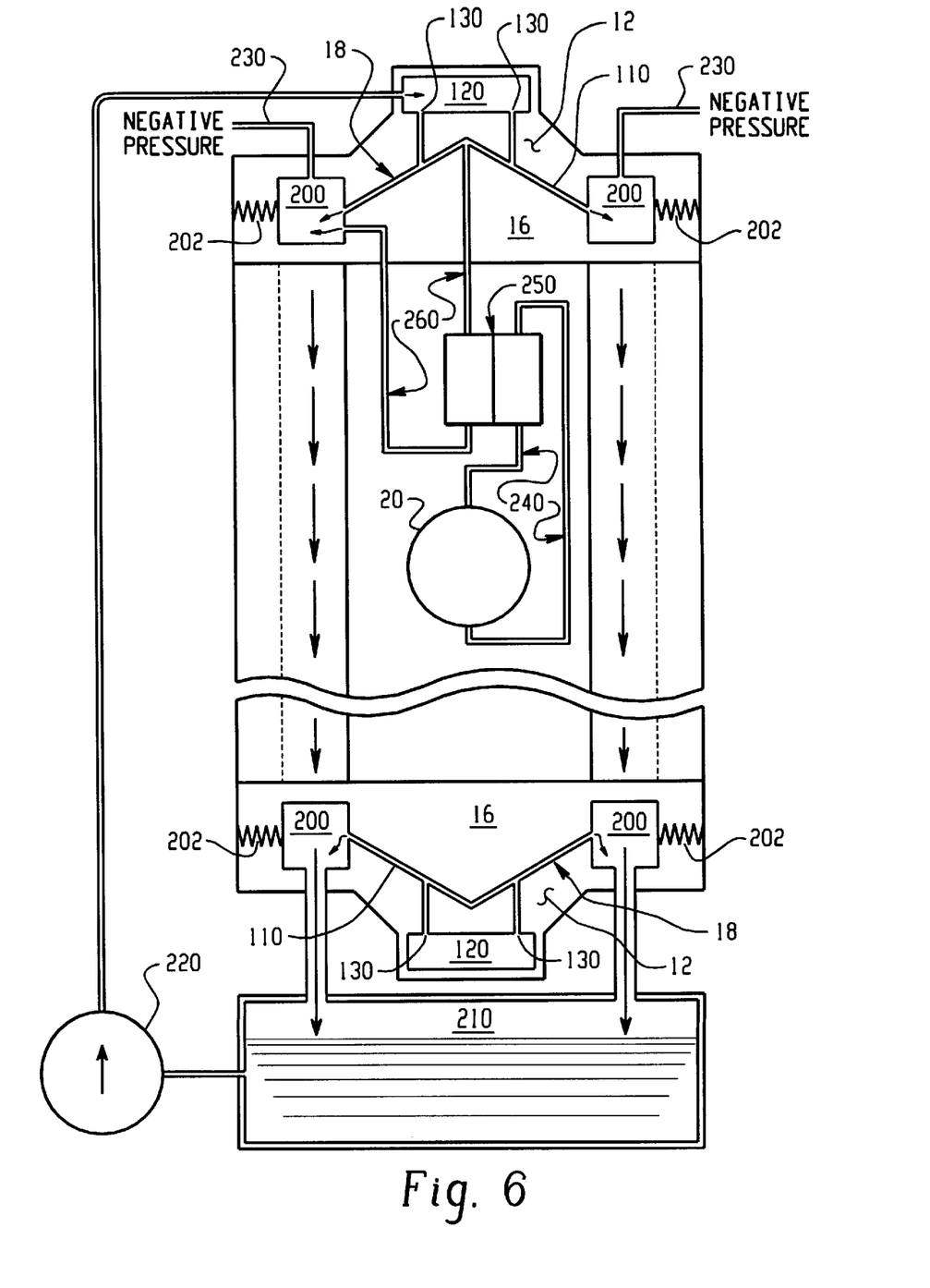

With further reference to FIG. 6, in an alternate embodiment preferably used in conjunction with a liquid fluid bearing 18, a fluid recovery system is employed to capture or collect fluid escaping or otherwise leaving the fluid bearing 18. The fluid recovery system includes a pair (front and back) of annular recovery chambers 200 which empty into a collection reservoir 210. Preferably, the annular recovery chambers 200 are housed inside and defined by non-contact bearing seals 202 at the front and back of the fluid bearing 18. The non-contact seals 202 serve to contain in the annular recovery chambers 200 fluid escaping the bearing 18 and to seal the bearing 18 from outside contaminants without providing physical contact between the stationary gantry 12 and the rotating gantry 16.

The bottoms of the annular recovery chambers 200 are open to the collection reservoir 210 such that gravity drains fluid which has trickled down to the bottom of the recovery chambers 200 from the same into the collection reservoir 210. Preferably, a fluid pump 220 pumps or recirculates the collected fluid from the collection reservoir 210 to the reservoir 120 where it is stored under pressure for feeding the fluid bearing 18. In a closed system or circulation loop, pumping fluid from the collection reservoir 210 creates a negative pressure which tends to draw or pull fluid from the recovery chambers 200. That, in turn, creates a negative pressure in the recovery chambers 200 which tends to draw or pull fluid from the bearing 18. In this manner, circulation of the fluid is encouraged.

Optionally, through ports, conduits, or the like, such as the depicted vacuum hoses 230, a negative pressure, preferably small, is applied to the annular recovery chambers with a vacuum pump or similar negative pressure producing apparatus (not shown). The negative pressure in the annular recovery chambers 200 further aids in maintaining the circulation of the bearing fluid buy promoting the draw or pull of fluid from the fluid bearing 18 into the annular recovery chambers 200.

In an alternate embodiment, the radiation source 20 (e.g., an x-ray tube) is fluid cooled, for example, by a liquid such as oil circulating in a cooling system. More specifically, the cooling system circulates a cooling fluid in a loop 240 past or over the radiation source 20 such that the cooling fluid absorbs heat generated by the operation of the radiation source 20 to thereby cool the same. To remove the absorbed heat from the cooling fluid, a heat exchanger 250 (e.g., a fluid to fluid heat exchanger) interfaces the cooling system with the recovery system. That is to say, the loop 240 of the cooling system circulates the cooling fluid through the heat exchanger 250 where heat from the cooling fluid is removed.

In the illustrated embodiment, the fluid recovery system also includes a circulation loop 260 which passes through the heat exchanger 250 wherein heat is transferred from the cooling fluid in loop 240 to the fluid in circulation loop 260. In the illustrated example, the circulation loop 260 saps, drains, or otherwise taps off fluid from the fluid bearing 18 and returns it to one or both of the annular recovery chambers 200. The fluid thereafter collected in the collection reservoir 210 is cooled via a separate heat exchanger (not shown) which is optionally remotely located.

In an alternate embodiment, the fluid supply system is supported on the rotating gantry 16 rather than the stationary gantry 12 as shown. That is to say, the reservoir 120, orifices 130, fluid distribution pads 140, etc., are supported on the rotating gantry 16. Preferably, the fluid bearing 18 having a rotating gantry side fluid supply system is gas or air based. While increasing the weight load on the rotating gantry 16, certain other advantages are achieved. Namely, space is conserved by mounting the fluid pump for supplying the reservoir 120 on the rotating gantry 16. Additionally, the pump is preferably positioned or mounted to counter balance the radiation source 20 and thereby provide even distribution of the weight on the rotating gantry 16.

In another alternative, at the interface of the gantries, the roles of the track (formed by surface 12a and 12b) and the follower/guide (formed by surfaces 16a and 16b) are optionally reversed. That is to say, a recessed track is optionally defined by or formed on the rotating gantry 16 while a protruding follower/guide is defined by or formed on the stationary gantry 12.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A CT scanner for obtaining a medical diagnostic image of a subject, said CT scanner comprising:
   a stationary gantry;
   a rotating gantry rotatably supported on the stationary gantry for rotation about the subject; and,
   a fluid bearing interposed between the stationary and rotating gantries, said fluid bearing providing a fluid barrier which separates the rotating gantry from the stationary gantry.

2. The CT scanner according to claim 1, wherein the fluid barrier is a gas.

3. The CT scanner according to claim 2, wherein the gas is air.

4. The CT scanner according to claim 1, wherein the fluid barrier is a liquid.

5. The CT scanner according to claim 4, wherein the liquid is oil.

6. A CT scanner comprising:

a fluid bearing interposed between a first gantry and a second gantry rotatable supported on the first gantry, said fluid bearing providing a fluid barrier which separates the second gantry from the first gantry; and, pads arranged on one of the first and second gantries at their interface, said pads having a beveled edge along a leading side thereof relative to a direction of rotation of the second gantry.

7. The CT scanner according to claim 6, wherein a fluid used to create the fluid barrier is supplied to the fluid bearing through the pads which distribute the fluid between the first and second gantries.

8. The CT scanner according to claim 7, said CT scanner further comprising:

a reservoir containing fluid, said fluid being supplied from the reservoir to the fluid bearing to create the fluid barrier.

9. A CT scanner comprising:

a fluid bearing interposed between a first gantry and a second gantry rotatable supported on the first gantry, said fluid bearing providing a fluid barrier which separates the second gantry from the first gantry;

wherein a shape of the fluid bearing is defined by two conic sections which meet at a plane to form an annular V-shaped trough.

10. The CT scanner according to claim 9, wherein the shape of the fluid bearing is symmetrical with respect to the plane which is normal to an axis of rotation of the second gantry.

11. A CT scanner comprising:

a fluid bearing interposed between a first gantry and a second rotating gantry rotatable supported on the first gantry, said fluid bearing providing a fluid barrier which separates the second rotating gantry from the first gantry; and, a recovery system which collects fluid escaping from the fluid bearing.

12. The CT scanner according to claim 11, said CT scanner further comprising:

a radiation source attached to the second rotating gantry, said radiation source producing a beam of penetrating radiation which irradiates a subject as the second rotating gantry rotates;

a cooling system which circulates a cooling fluid past the radiation source, said cooling fluid drawing heat from the radiation source as the cooling fluid is circulated past the radiation source; and, a heat exchanger interfacing the cooling system with the recovery system, said heat exchanger transferring heat from the cooling fluid in the cooling system to the fluid collected by the recovery system.

13. The CT scanner according to claim 11, wherein the recovery system returns fluid collected thereby to the fluid bearing.

14. A method of rotating a source of radiation about an axis, said method comprising:

(a) suspending a second gantry from a first gantry, said second gantry having the source of radiation mounted thereto;

(b) feeding a fluid in between the first and second gantries such that they are spaced apart from one another by a layer of the fluid; and, (c) rotating the second gantry.

15. The method according to claim 14, said method further comprising:

controlling a rate at which the fluid is fed in between the first and second gantries.

16. The method according to claim 14, said method further comprising:

storing a reserve of the fluid such that the fluid is fed inbetween the first and second gantries from the stored reserve.

17. A method of rotating a source of radiation about an axis, said method comprising:

(a) suspending a second gantry from a first gantry, said second gantry having the source of radiation mounted thereto;

(b) feeding a fluid in between the first and second gantries such that they are spaced apart from one another by a layer of the fluid;

(c) rotating the second gantry; and, (d) generating hydro-dynamic forces which radially stabilize the second gantry as it rotates.

18. A method of rotating a gantry about an axis, said method comprising:

(a) suspending a second gantry from a first gantry;

(b) feeding a fluid in between the first and second gantries such that they are spaced apart from one another by a layer of the fluid;

(c) rotating the second gantry;

(d) collecting the fluid as it escapes from in between the first and second gantries; and, (e) returning the fluid for further use.

19. The method according to claim 18, said method further comprising:

transferring heat from a cooling fluid on the second gantry to the collected fluid.

* * * * *